United States Patent [19]

Buschmann et al.

[11] Patent Number: 5,071,851

[45] Date of Patent: Dec. 10, 1991

[54] FUNGICIDAL CYCLOHEXYLAMINES

[75] Inventors: Ernst Buschmann, Ludwigshafen; Norbert Goetz, Worms; Bernhard Zipperer, Dirmstein; Eberhard Ammermann, Ludwigshafen; Ernst-Heinrich Pommer, Limburgerhof, all of Fed. Rep. of Germany

[73] Assignee: BASF Aktiengesellschaft, Ludwigshafen, Fed. Rep. of Germany

[21] Appl. No.: 549,241

[22] Filed: Jul. 9, 1990

Related U.S. Application Data

[63] Continuation of Ser. No. 127,417, Dec. 2, 1987, abandoned.

[30] Foreign Application Priority Data

Dec. 17, 1986 [DE] Fed. Rep. of Germany ....... 3643009

[51] Int. Cl.$^5$ .................. A61K 31/535; A61K 31/38; A61K 31/435; A61K 31/40; C07D 265/30
[52] U.S. Cl. .............. 514/238.8; 514/231.2; 514/239.2; 514/239.5; 514/227.5; 514/212; 514/255; 514/317; 514/428; 514/429; 544/158; 544/170; 544/177; 544/59; 544/401; 544/403; 540/609; 540/612; 546/192; 546/240; 548/570; 548/574
[58] Field of Search ...................... 544/158, 170, 177; 514/238.8, 239.2, 239.5, 231.2

[56] References Cited

U.S. PATENT DOCUMENTS 4,636,382 1/1987 Hernestain et al. ................ 544/158

FOREIGN PATENT DOCUMENTS 0029617 6/1981 European Pat. Off. ............ 544/158
1214471 1/1965 Fed. Rep. of Germany ...... 544/158
3321712 6/1983 Fed. Rep. of Germany ...... 544/158

OTHER PUBLICATIONS

Chemical Abstracts, vol. 63, No. 1, 1783–1784 (1965).

Primary Examiner—Johann Richter
Attorney, Agent, or Firm—Oblon, Spivak, McClelland, Maier & Neustadt

[57] ABSTRACT 4-substituted cyclohexylamines of the formula

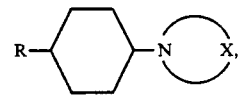

I where R is the group $CR^1R^2R^3$, where $R^1$, $R^2$ and $R^3$ are hydrogen, unsubstituted or substituted alkyl, alkoxy, alkylthio or cycloalkyl, with the proviso that at most one of the substituents $R^1$, $R^2$ and $R^3$ is hydrogen, X is an alkylene group which, together with the N atom, forms a substituted or unsubstituted heterocyclic ring in which up to 2 carbon atoms may be replaced by O, N or S atoms, and salts thereof, and fungicides containing these compounds.

6 Claims, No Drawings

FUNGICIDAL CYCLOHEXYLAMINES

This application is a continuation of application Ser. No. 07/127,417, filed on Dec. 2, 1987, now abandoned.

The present invention relates to tertiary, 4-substituted cyclohexylamines, processes for their manufacture, their use as fungicides, fungicidal compositions and methods of combating injurious fungi with these active ingredients.

The use of N-cyclododecyl-2,6-trans-dimethylmorpholine as a fungicide has been disclosed (DE 3 321 712). The use of N-(4'-cyclohexylcyclohexyl)-2,6-dimethylmorpholine as a fungicide has also been disclosed C.A. No. 1541-88-4). Alkyl-substituted N-cyclohexyl-2,6-dimethylmorpholines having a fungicidal action are also known (DE 1 214 471). However, their fungicidal action, and especially the spectrum of action, is not satisfactory.

We have now found that cyclohexylamines substituted in the 4-position and having the formula I

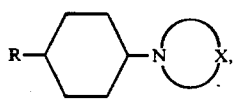

where R is the group $CR^1R^2R^3$ with a total of 6-20 carbon atoms and in which $R^1$, $R^2$ and $R^3$ are identical or different and each denotes hydrogen, branched or straight-chain, unsubstituted or hydroxy- or $C_6$-cycloalkyl-substituted $C_1$-$C_8$-alkyl, $C_1$-$C_8$-alkoxy, $C_1$-$C_8$-alkylthio or $C_3$-$C_6$-cycloalkyl, with the proviso that at most one of the substituents $R^1$, $R^2$ and $R^3$ is hydrogen, and X is an alkylene group of 4 to 6 carbon atoms which, together with the nitrogen atom, forms a 5-to 7-membered heterocyclic ring in which up to 2 carbon atoms may be replaced by O, N or S atoms and which may be substituted by 1 to 3 branched or straight-chain alkyl or aralkyl radicals, each of 1 to 10 carbon atoms, and salts thereof, are well tolerated by plants and have a broad spectrum of fungicidal action.

By "salts", we mean plant-tolerated salts of any inorganic or organic acid, e.g., hydrochloric acid, hydrobromic acid, sulfuric acid, nitric acid, acetic acid, higher fatty acids, e.g., palmitic acid, and arylsulfonic acids, e.g., dodecylbenzenesulfonic acid.

The group $CR^1R^2R^3$ denotes for example n-hex-2-yl, n-hex-3-yl, 2-methylpent-2-yl, 2,4,4-trimethylpent-2-yl, 2-methylhex-2-yl, 2-methylhept-2-yl, 2,4-dimethylpent-2-yl, 1-cyclohexylethyl, 2-cyclohexylprop-2-yl, 1-cyclohexylprop-2-yl, 4-cyclohexylbut-2-yl, 4-cyclohexyl-2-methylbut-2-yl, and 2-ethoxybut-2-yl.

The group X denotes for instance, together with the nitrogen atom whose substituent it is, pyrrolidine, mono-, di- or trimethylpyrrolidine, piperidine, mono-, di-, tri- or tetramethylpiperidine, ethylpiperidine, propylpiperidine, tert-butylpiperidine, benzylpiperidine, morpholine, mono-, di- or trimethylmorpholine, thiomorpholine, dimethylthiomorpholine, piperazine, ethylpiperazine, propylpiperazine, tert-butylpiperazine, and hexamethyleneimine.

The novel amines of the formula I may contain chiral centers. They are generally obtained as racemates and in some instances as diastereomer mixtures. Single diastereomers may be obtained in pure form for example by distillation, column chromatography or on the basis of solubility differences. Single racemates and enantiomers may be obtained from such purified diastereomers by conventional methods. All these compounds and mixtures are encompassed by the present invention. Both the single diastereomers and enantiomers and the mixtures thereof obtained on synthesis are suitable for the use of the novel amines as fungicides. Mixtures are preferred.

The novel amines may for example be obtained by reacting the corresponding primary amines of the formula II with bifunctional alkylating agents. Examples of suitable alkylating agents are 1,4-dicloro(dibromo)butane, 1,5-dichloro(dibromo)pentane, 1,6-dichloro(dibromo)hexane, di-(2-chloroethyl)ether, di-(2-chloroethyl)sulfide, di-(2-chloroethyl)amine, di-(2-chloroethyl)methyl-(or -ethyl-, -propyl- or -tert-butyl-)amine, di-(1-chloro-2-propyl)ether, di-(1-chloro-2-propyl)sulfide, di-(1-chloro-2-propyl)methyl(or -ethyl-, -propyl- or -tert-butyl-)amine.

Alkylation is carried out in a diluent and in the presence of an auxiliary base. Examples of suitable diluents are polar solvents such as methanol, ethanol, propanols, butanols, cyclohexanol, acetone, methyl ethyl ketone, acetonitrile, dimethylformamide, N-methylpyrrolidone, ethyl acetate, nitromethane, dimethyl sulfoxide, dioxane and tetrahydrofuran.

All conventional acid binders may be used as auxiliary bases for the reaction to give amines of the formula I. Alkali metal and alkaline earth metal oxides, hydroxides and carbonates, tertiary amines and basic ion exchangers are preferred.

Examples of basic compounds are potassium hydroxide, sodium hydroxide, calcium hydroxide, barium hydroxide, magnesium oxide, potassium carbonate, sodium carbonate, triethylamine, tri-n-propylamine, tri-n-butylamine, ethyldiisopropylamine, N,N-dimethylcyclohexylamine, pyridine, methylpyridines, quinoline, isoquinoline, 2,6-lutidine, and 2,4,6-collidine.

The amines may also be prepared by alkylating the corresponding primary amines II (if desired, in stages) with oxiranes, and cyclizing the bis-($\beta$-hydroxyalkyl)amines to the corresponding morpholines.

Preferred oxiranes are ethylene oxide, propylene oxide and isobutylene oxide. Alkylation is advantageously carried out in the presence of catalytic or stoichiometric amounts of a proton source, e.g., water, ethanol, 1- or 2-propanol, n- or tert-butanol, at from 0° to 150° C., preferably from 20° to 100° C., and at atmospheric or superatmospheric pressure.

The bis-($\beta$-hydroxyalkyl)amines are advantageously cyclized to the morpholines according to the invention in the presence of a strong acid, e.g., sulfuric acid, and preferably at from 50° to 150° C.

The amines may also be prepared by reacting the corresponding cyclohexanones III with secondary amines of the formula IV to give enamines, which are then hydrogenated to give the amines I, or the corresponding cyclohexanones III are converted direct to the amines I with the secondary amines IV in the presence of a reducing agent.

The cyclohexanones III are known and may be obtained by conventional processes, e.g., from the corresponding phenols.

The cyclic secondary amines IV are known and many of them are commercially available.

The conditions for manufacturing enamines from the cyclohexanones III and the secondary amines IV have been disclosed in the literature (for example J. Smuskovicz, Enamines, Adv. Org. Chem., 4, 1 (1963); A. G. Cook, Enamines, M. Dekker, New York, 1969; Houben-Weyl, Methoden der Org. Chemie, vol. XI/1, 1957, p. 170 et seq.).

The same applies to the hydrogenation of the enamines to the corresponding amines.

The cyclohexanones III are directly aminated with the secondary amines IV in the presence of a reducing agent in accordance with known methods to give the amines I according to the invention.

Examples of reducing agents are particularly hydrogen (Houben-Weyl, Methoden der Org. Chemie, vol. XI/1, 1957, p. 602 et seq.), formic acid (ibid., p. 648 et seq.) and complex hydrides, preferably sodium cyanoborohydride (Synthesis, 1975, 135; Org. Prep. Procd. Int. 11 (1979) 201).

EXAMPLE 1

2,6-Dimethyl-4-[4-(2-cyclohexylprop-2-yl)-cyclohexyl]-morpholine 41.4 g (0.3 mole) of potassium carbonate is added to a solution of 23.3 g (0.1 mole) of 4-(2-cyclohexylprop-2-yl)-cyclohexylamine and 17.1 g (0.1 mole) of di-(1-chloro-2-propyl)-ether in 200 ml of cyclohexanol, and the mixture is refluxed for 8 hours while stirring. After cooling, approx. 100 ml of water is added, and the organic phase is separated and dried over a small amount of $Na_2SO_4$. The residue remaining after the cyclohexanol has been distilled off is fractionally distilled under reduced pressure. At 160°-164° C./0.2 mm there is obtained 16 g (50% of theory) of the captioned compound as a colorless oil (isomer mixture; compound no. 1).

EXAMPLE 2

2,6-dimethyl-4-[4-(1,1,3,3-tetramethylbutyl)-cyclohex-1-yl]-morpholine

At 60°-70° C. and while stirring, 240 g (4.0 moles) of propylene oxide is dripped into 211 g (1.0 mole) of 4-(1,1,3,3-tetramethylbutyl)-cyclohexylamine (cis-trans mixture) and 6 g (0.33 mole) of water. The mixture is heated to 90°-95° C. and every 8 hours (7 times in all) 116 g (2.0 moles) of propylene oxide is added. The reaction can be monitored gas-chromatographically.

Without any further working up, distillation is carried out under reduced pressure in a fractionation column. At 190°-195° C./0.6 mm approx. 200 g of a 9:1 mixture of bis-(2-hydroxypropyl)-4-(1,1,3,3-tetramethylbutyl)-cyclohexylamine and the monoalkylated amine pass over. Renewed distillation gives 171 g of pure tertiary amine.

The same amount by weight of conc. sulfuric acid is added and the mixture is stirred for 4 hours at 100°-110° C. While cooling, diluted NaOH is added to bring the pH to 12; the morpholine is then extracted several times with dichloromethane. The dried organic phase is concentrated and distilled under reduced pressure. There is obtained 120 g of the captioned compound as a colorless oil of b.p. 165°-168° C./2 mm (approx. 39% of theory; compound no. 2).

The following compounds may be obtained analogously:

TABLE

| Ex. no | $R^1$ | $R^2$ | $R^3$ | X | Physical data (b.p./m.p.) |
| --- | --- | --- | --- | --- | --- |
| 1 | $CH_3$ | $CH_3$ | cyclo-$C_6H_{11}$ | —$CH_2CH(CH_3)OCH(CH_3)CH_2$ | 160-164° C./0.2 mm |
| 2 | $CH_3$ | $CH_3$ | $(CH_3)_3CCH_2$ | —$CH_2CH(CH_3)OCH(CH_3)CH_2$— | 165-168° C./2.0 mm |
| 3 | $CH_3$ | $CH_3$ | cyclo-$C_6H_{11}$ | —$CH_2CH_2OCH_2CH_2$— | |
| 4 | $CH_3$ | $CH_3$ | cyclo-$C_6H_{11}$ | —$(CH_2)_6$— | |
| 5 | $CH_3$ | $CH_3$ | cyclo-$C_6H_{11}$ | —$(CH_2)_5$— | |
| 6 | $CH_3$ | $CH_3$ | cyclo-$C_6H_{11}$ | —$(CH_2)_4$— | |
| 7 | $CH_3$ | $CH_3$ | $(CH_3)_3CCH_2$ | —$CH_2CH_2OCH_2CH_2$— | |
| 8 | $CH_3$ | $CH_3$ | $(CH_3)_3CCH_2$ | —$(CH_2)_6$— | |
| 9 | $CH_3$ | $CH_3$ | $(CH_3)_3CCH_2$ | —$(CH_2)_5$— | |
| 10 | $CH_3$ | $CH_3$ | $(CH_3)_3CCH_2$ | —$(CH_2)_4$— | |
| 11 | $CH_3$ | $CH_3$ | $CH_3CH(CH_3)CH_2$ | —$(CH_2)_4$— | |
| 12 | $CH_3$ | $CH_3$ | $CH_3CH(CH_3)CH_2$ | —$(CH_2)_5$— | |
| 13 | $CH_3$ | $CH_3$ | $CH_3CH(CH_3)CH_2$ | —$(CH_2)_6$— | |
| 14 | $CH_3$ | $CH_3$ | $CH_3CH(CH_3)CH_2$ | —$CH_2CH_2OCH_2CH_2$— | |
| 15 | $CH_3$ | $CH_3$ | $CH_3CH(CH_3)CH_2$ | —$CH_2CH(CH_3)OCH(CH_3)CH_2$— | 148-154° C./0.4 mm |
| 16 | $CH_3$ | $CH_3$ | n-$C_5H_{11}$ | —$CH_2CH(CH_3)OCH(CH_3)CH_2$— | 156-160° C./0.7 mm |
| 17 | $CH_3$ | $CH_3$ | n-$C_5H_{11}$ | —$CH_2CH_2OCH_2CH_2$— | |
| 18 | $CH_3$ | $CH_3$ | n-$C_5H_{11}$ | —$(CH_2)_6$— | |
| 19 | $CH_3$ | $CH_3$ | n-$C_5H_{11}$ | —$(CH_2)_5$— | |
| 20 | $CH_3$ | $CH_3$ | n-$C_5H_{11}$ | —$(CH_2)_4$— | |
| 21 | cyclo-$C_6H_{11}CH_2CH_2$ | $CH_3$ | H | —$(CH_2)_4$— | |
| 22 | cyclo-$C_6H_{11}CH_2CH_2$ | $CH_3$ | H | —$(CH_2)_5$— | |
| 23 | cyclo-$C_6H_{11}CH_2CH_2$ | $CH_3$ | H | —$(CH_2)_6$— | |
| 24 | cyclo-$C_6H_{11}CH_2CH_2$ | $CH_3$ | H | —$CH_2CH_2OCH_2CH_2$— | |
| 25 | cyclo-$C_6H_{11}CH_2CH_2$ | $CH_3$ | H | —$CH_2CH(CH_3)OCH(CH_3)CH_2$— | 170° C./0.3 mm |

In general terms, the novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
Rhizoctonia species in cotton,
Ustilago species in cereals and sugar cane,

*Venturia inaequalis* (scab) in apples,
*Pyrenophora teres* in barley,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
*Plasmopara viticola* in grapes, and
Fusarium and Verticillium species in various plants.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicides generally contain from 0.1 to 95, and preferably from 0.5 to 90, wt % of active ingredient.

The application rates are from 0.02 to 3 kg or more of active ingredient per hectare, depending on the type of effect desired. The novel compounds may also be used for protecting materials for instance against *Paecilomyces variotii.*

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 1 is mixed with 10 parts by weight of N-methyl-α-pyrrolidone. A mixture is obtained which is suitable for application in the form of very fine drops.

II. 20 parts by weight of compound no. 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 15 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 25 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 16 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 15 is intimately mixed with 97 parts by weight of particulate kaolin. A dust is obtained containing 3% by weight of the active ingredient.

VII. 30 parts by weight of compound no. 15 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 1 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 2 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in a greater fungicidal action spectrum.

The following list of fungicides with which the novel compounds may be combined is intended to illustrate possible combinations but not to impose any restrictions.

Examples of fungicides which may be combined with the novel compounds are:

sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate, ammonia complex of zinc N,N'-propylenebisdithiocarbamate,
zinc N,N'-propylenebisdithioccarbamate and
N,N'-polypropylenebis(thiocarbamyl) disulfide;

nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;

heterocyclic substances, such as
2-heptadecylimidazol-2-yl acetate,
2,4-dichloro-6-(o-chloroanilino)-s-triazine,
0,0-diethyl phthalimidophosphonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenyl-sulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene, and various fungicides, such as dodecylguanidine acetate,
3-[3-(3,5-dimethyl-2-oxycyclohexyl)-2-hydroxyethyl]-glutaramide, hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

USE EXAMPLES

The prior art compounds used for comparison purposes were N-cyclododecyl-2,6-trans-dimethylmorpholine (A), and N-(4'-cyclohexylcyclohexyl)-2,6-dimethylmorpholine (B).

USE EXAMPLE 1

Action on *Pyrenophora teres*

Barley seedlings of the "Asse" variety were sprayed, at the 2-leaf stage, to runoff with aqueous suspensions consisting (dry basis) of 80 wt % of active ingredient and 20 wt % of emulsifier. After 24 hours, the plants were inoculated with a spore suspension of the fungus *Pyrenophora teres* and placed for 48 hours in a high-humidity climatic cabinet at 18° C. The plants were then cultivated for a further 5 days in the greenhouse at 20° to 22° C. and a relative humidity of 70%. The extent of fungus spread was then assessed.

The results show that a 0.05 wt % spray liquor of, for example, compounds nos. 1, 2, 15 and 25 had a very good action (90%), whereas prior art compound B was ineffective (0%).

USE EXAMPLE 2

Action on Wheat Brown Rust

Leaves of pot-grown wheat seedlings of the "Frühgold" variety were dusted with spores of brown rust (*Puccinia recondita*). The pots were then placed for 24 hours at 20° to 22° C. in a high-humidity (90-95%) chamber. During this period the spores germinated and the germ tubes penetrated the leaf tissue. The infected plants were then sprayed to runoff with aqueous liquors containing (dry basis) 80% of active ingredient and 20% of emulsifier. After the sprayed-on layer had dried, the plants were set up in the greenhouse at 20° to 22° C. and a relative humidity of 65 to 70%. The extent of rust fungus spread on the leaves was assessed after 8 days.

In this experiment, the fungicidal action after treatment with a 0.025% formulation of, for example, compounds nos. 1, 2, 15 and 25 was very good (90%), whereas the action of comparative agents A and B was only moderate (60%).

USE EXAMPLE 3

Action on Wheat Mildew

Leaves of pot-grown wheat seedlings of the "Frühgold" variety were sprayed with aqueous liquors containing (dry basis) 80% of active ingredient and 20% of emulsifier, and sprayed, 24 hours after the sprayed-on layer had dried, with spores of wheat mildew (*Erysiphe graminis* var. tritici). The plants were then set up in the greenhouse at 20° to 22° C. and a relative humidity of 75 to 80%. The extent of mildew spread was assessed after 7 days.

In this experiment, a 0.0125% formulation of, for example, compounds nos. 1, 2, 15 and 16 had a very good fungicidal action (90%), whereas comparative agents A and B only had a moderate action (60%).

We claim:

1. A 4-substituted cyclohexylamine of the formula I

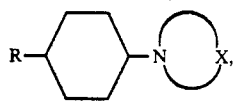

where R is the group $CR^1R^2R^3$ with a total of 6-20 carbon atoms and in which $R^1$, $R^2$ and $R^3$ are identical of different and each denotes branched or straight-chain, unsubstituted or hydroxy- or $C_6$-cycloalkyl-substituted $C_1$-$C_8$-alkyl, $C_1$-$C_8$-alkoxy, $C_1$-$C_8$-alkylthio or $C_3$-$C_6$-cycloalkyl, and

is a morpholine which is unsubstituted or which is substituted by 1 to 3 branched or straight-chain alkyl or aralkyl radicals, each of 1 to 10 carbon atoms, and salts thereof.

2. A compound as set forth in claim 1, wherein $R^1$ and $R^2$ are methyl, $R^3$ is the radical $CH_2C(CH_3)_3$ or cyclohexyl, and X is the radical —$CH_2$—$CH(CH_3)$—O—$CH(CH_3)$—$CH_2$—.

3. A compound as set forth in claim 1, wherein $R^1$ and $R^2$ are methyl, $R^3$ is the radical $CH_2CH(CH_3)_2$ or n-pentyl, and X is the radical —$CH_2$—$CH(CH_3)$—O—$CH(CH_3)$—$CH_2$—.

4. A compound as set forth in claim 1, wherein said morpholine is a mono-, di or trimethylmorpholine.

5. A fungicidal composition containing a fungicidally effective amount of a 4-substituted cyclohexylamine of of the formula I

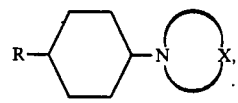

where R is the group $CR^1R^2R^3$ with a total of 6-20 carbon atoms and in which $R^1$, $R^2$ and $R^3$ are identical or different and each denotes branched or straight-chain, unsubstituted or hydroxy- or $C_6$-cycloalkyl-substituted $C_1$-$C_8$-alkyl, $C_1$-$C_8$-alkylthio or $C_2$-$C_6$-cycloalkyl, and

is a morpholine which is unsubstituted or which is substituted by 1 to 3 branched or straight-chain alkyl or aralkyl radicals, each of 1 to 10 carbon atoms, or a salt thereof, and aolid or liquid carrier.

6. A method for combating fungi, wherein a fungi, or a material, area, plant or seed threatened by fungus attack, is contacted with a fungicidally effective amount of a 4-substituted cyclohexylamine of the formula I where R is the group $CR^1R^2R^3$ with a total of 6-20 carbon atoms and in which $R^1$, $R^2$ and R3 are identical or different and each denotes branched or straight-chain, unsubstituted or hydroxy- or $C_6$-cycloalkyl-substituted $C_1$-$C_8$-alkyl, $C_1$-$C_8$-alkoxy, $C_1$-$C_8$-alkylthio, or $C_3$-$C_6$-cycloalkyl, and is a morpholine which is unsubstituted or which is substituted by 1 to 3 branched or straight-chain alkyl or aralkyl radicals, each of 1 to 10 carbon atoms, or a salt thereof.

* * * * *